United States Patent [19] [11] Patent Number: 5,075,316
Hubele [45] Date of Patent: Dec. 24, 1991

[54] PEST CONTROL COMPOSITIONS

[75] Inventor: Adolf Hubele, Magden, Switzerland

[73] Assignee: Ciba-Geigy Corporation, Ardsley, N.Y.

[21] Appl. No.: 496,480

[22] Filed: Mar. 20, 1990

[30] Foreign Application Priority Data

Mar. 22, 1989 [CH] Switzerland ............. 1073/89
Oct. 17, 1989 [CH] Switzerland ............. 3771/89

[51] Int. Cl.$^5$ ............. C07D 239/48; C07D 239/42; C07D 413/12; A01N 43/54
[52] U.S. Cl. ............. 514/275; 544/321; 544/324; 544/331; 544/122; 544/123; 544/60; 544/295; 544/182; 544/216; 544/217; 544/218; 544/219; 544/96; 544/98; 514/272; 514/241; 514/245; 514/229.5; 514/242; 514/252; 514/227.2; 514/227.8; 514/226.8; 514/235.8
[58] Field of Search ............. 514/269, 272, 275, 235.8, 514/227.8, 241, 242, 226.8; 544/321, 323, 330, 332, 60, 122, 123, 182, 218, 98

[56] References Cited

U.S. PATENT DOCUMENTS 4,897,396 1/1990 Hubele ............. 514/275

FOREIGN PATENT DOCUMENTS 0224339 6/1987 European Pat. Off. .
0295210 12/1988 European Pat. Off. .
1518122 2/1968 France .
151404 10/1981 German Democratic Rep. .

Primary Examiner—John M. Ford
Attorney, Agent, or Firm—George R. Dohmann; Edward McC. Roberts

[57] ABSTRACT

Novel compounds of the formula

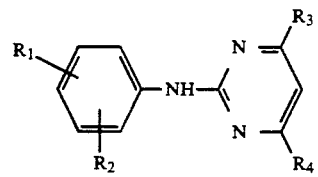

in which: $R_1$ and $R_2$ independently of one another are hydrogen, halogen, $C_1$-$C_3$alkyl, $C_1$-$C_2$halogenoalkyl, $C_1$-$C_3$alkoxy or $C_1$-$C_3$halogenoalkoxy; $R_3$ is $C_3$-$C_6$cycloalkyl or $C_3$-$C_6$cycloalkyl which is substituted by up to three identical or different methyl or halogen groups; $R_4$ is halogen, thiocyano, —$OR_5$, —$SR_5$ or —$NR_5R_6$, in which $R_5$ and $R_6$ are halogen groups; $R_4$ is halogen, thiocyano, —$OR_5$, —$SR_5$ or —$NR_5R_6$, in which $R_5$ and $R_6$ are as defined herein, are novel active compounds for preventing attack of plants by microorganisms. The compounds can be employed as microbicides as such or in the form of suitable agents.

20 Claims, No Drawings

PEST CONTROL COMPOSITIONS

The present invention relates to 2-anilino-pyrimidine derivatives of the following formula I, the preparation of these substances and agrochemical compositions which contain at least one of these compounds as the active substance. The invention also relates to the preparation of the compositions mentioned and the use of the active substances or compositions for controlling pests, especially microorganisms, preferably fungi, which are harmful to plants.

The compounds according to the invention are those of the general formula I

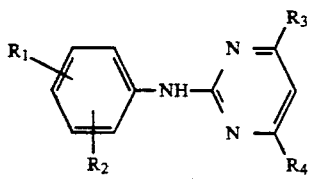

in which: $R_1$ and $R_2$ independently of one another are hydrogen, halogen, $C_1$–$C_3$alkyl, $C_1$–$C_2$halogenoalkyl, $C_1$–$C_3$alkoxy or $C_1$–$C_3$halogenoalkoxy; $R_3$ is $C_3$–$C_6$cycloalkyl or $C_3$–$C_6$cycloalkyl which is substituted by up to three identical or different methyl or halogen groups; $R_4$ is halogen, thiocyano(—SCN), —$OR_5$, —$SR_5$ or —$NR_5R_6$, in which $R_5$ a) is hydrogen, unsubstituted $C_1$–$C_8$alkyl or a $C_1$–$C_4$alkyl group which is substituted by halogen, hydroxyl, cyano, $C_1$–$C_4$alkoxy, $C_1$–$C_4$alkylamino, bis($C_1$–$C_4$alkyl)amino or $C_3$–$C_6$cycloalkyl or by substituted or unsubstituted phenyl or by —CO—$OC_1$—$C_3$alkyl; or b) is $C_3$–$C_6$cycloalkyl which is unsubstituted or substituted by methyl; or c) is $C_3$–$C_6$alkenyl which is unsubstituted or substituted by halogen; or d) is $C_3$–$C_6$alkinyl which is unsubstituted or substituted by halogen; or e) is phenyl which is unsubstituted or substituted by halogen, $C_1$–$C_3$alkyl, $C_1$–$C_3$alkoxy or nitro; or f) is a 5-membered or 6-membered heterocyclic radical which is bonded via —$CH_2$— if appropriate, contains one to three hetero atoms N, O or S and is unsubstituted or substituted by halogen, $C_1$–$C_3$alkyl, $C_1$–$C_3$alkoxy or nitro; or g) is an acyl radical —CO—R', in which R' is $C_1$–$C_6$alkyl which is unsubstituted or substituted by halogen or $C_1$–$C_3$alkoxy; $C_3$–$C_6$alkenyl which is unsubstituted or substituted by halogen; or phenyl which is unsubstituted or substituted by halogen, $C_1$–$C_3$alkyl, $C_1$–$C_3$alkoxy or nitro; or h) is a carbamoyl radical —CO—NH—R'' or an oxycarbonyl radical —CO—OR'', in which R'' is an aliphatic or cycloaliphatic radical having not more than 6 C atoms, which is unsubstituted or halogen-substituted, or in which R'' is a phenyl or benzyl radical, which is in each case unsubstituted or substituted in the aromatic ring by halogen, $C_1$–$C_3$alkyl, $C_1$–$C_3$alkoxy or nitro; and in which $R_6$ is hydrogen, unsubstituted $C_1$–$C_8$alkyl or $C_1$–$C_4$alkyl which is substituted by halogen, hydroxyl, cyano or $C_1$–$C_4$alkoxy; or in which $R_6$ is $C_3$–$C_6$cycloalkyl which is unsubstituted or substituted by methyl; $C_3$–$C_6$alkenyl or $C_3$–$C_6$alkinyl which is in each case unsubstituted or substituted by halogen; or phenyl which is unsubstituted or substituted by halogen, $C_1$–$C_3$alkyl, $C_1$–$C_3$alkoxy or nitro; and wherein, in the case where $R_4$=$NR_5R_6$, the substituents $R_5$ and $R_6$, together with the N atom, can also together form an aziridine ring or a 5- or 6-membered heterocyclic radical, which can also contain one or two hetero atoms N, O or S in addition to the N atom and can be alkyl-substituted.

Alkyl by itself or alkyl as a constituent of another substituent, such as halogenoalkyl, alkoxy or halogenoalkoxy, is to be understood as meaning, for example, depending on the stated number of carbon atoms, methyl, ethyl, propyl, butyl, pentyl, hexyl, heptyl, octyl and their isomers, for example isopropyl, isobutyl, isoamyl, tert-butyl or sec-butyl.

An aliphatic radical is to be understood as meaning either an alkyl, alkenyl or alkinyl group. A cycloaliphatic radical is accordingly to be understood as meaning a saturated or unsaturated cyclic hydrocarbon radical.

$C_3$–$C_6$-Alkenyl is an aliphatic radical having a double bond, for example allyl, methallyl, crotyl, butenyl, pentenyl and the like.

A $C_3$–$C_6$alkinyl radical contains a triple bond, for example propargyl, propin-1-yl, butinyl and the like.

Halogen is fluorine, chlorine, bromine or iodine.

Halogenoalkyl and halogenoalkoxy are mono- to perhalogenated radicals, for example $CHCl_2$, $CH_2F$, $CCl_3$, $CH_2Cl$, $CHF_2$, $CF_3$, $CH_2CH_2Br$, $C_2Cl_5$, $CHBr$, $CHBrCl$ and the like, preferably $CF_3$ and $CHF_2$.

Cycloalkyl is, for example, depending on the number of carbon atoms mentioned, cyclopropyl, cyclobutyl, cyclopentyl or cyclohexyl.

In a substituted phenyl ring, 1 to 5, preferably 1 to 3, identical or different substituents chosen from halogen, $C_1$–$C_3$alkyl, $C_1$–$C_3$alkoxy and nitro can occur, it being obvious to the expert that not more than three substituents which tend towards decomposition, such as nitro, and spatially bulky substituents, such as isopropyl or iodine, can be present.

Examples of heterocylic radicals of the group —$NR_5R_6$ are imidazole, oxazole, thiazole, 1,2,4-triazole, pyrrole, pyrrolidine, piperidine, morpholine, thiomorpholine, 2,6-dimethylmorpholine and the like.

Further examples of $R_5$ by itself of the type defined are the abovementioned heterocyclic radicals, which are also bonded via carbon, and furthermore also furan, tetrahydrofuran (=THF), thiophene, pyridine, picoline, pyrazine, triazine, oxazine, dioxane and the like.

N-Pyrimidinylaniline compounds are already known. EP-A-0,224,339 and East German Patent Specification 151,404 thus describe compounds which have an N-2-pyrimidinyl structure as being active against fungi which are harmful to plants. However, the compounds known have not to date been able to satisfy the requirements imposed on them in practice. The compounds of the formula I according to the invention differ characteristically from the known compounds by the introduction of specific substituents $R_3$ and $R_4$ and combination thereof in the anilinopyrimidine structure, an unexpectedly high microbicidal activity being achieved with the novel compounds.

The compounds of the formula I are stable oils, resins or solids at room temperature. They can be employed preventively and curatively in the agricultural sector or in related fields for controlling microorganisms which are harmful to plants. Used at low concentrations, the active substances of the formula I according to the invention are distinguished not only by outstanding fungicidal action but also by particularly good plant tolerance.

One important group comprises those of the formula I in which $R_1$ and $R_2$ independently of one another are hydrogen or fluorine.

A particular group comprises the following compounds of the formula I in which $R_1$ and $R_2$ independently of one another are hydrogen, halogen, $C_1$-$C_3$alkyl, $C_1$-$C_2$halogenoalkyl, $C_1$-$C_3$alkoxy or $C_1$-$C_3$halogenoalkoxy; $R_3$ is $C_3$-$C_4$cycloalkyl, which is unsubstituted or monosubstituted by methyl or halogen; and $R_4$ is halogen, $-OR_5$ or $-NR_5R_6$, in which $R_5$ has the meanings a),b),c),d) or g) and $R_6$ is hydrogen or an alkyl, alkenyl or alkinyl radical, which can be unsubstituted or halogen-substituted if appropriate; or in which $R_5$ and $R_6$, together with the common N atom, are an aziridine ring or a piperidine or morpholine ring, which is unsubstituted or methyl-substituted if appropriate (=compound group Ib).

Amongst the abovementioned compounds, those in which $R_1$ and $R_2$ independently of one another are hydrogen or fluorine are preferred (=compound group Ibb).

Another important group comprises those compounds of the formula I in which: $R_1$ and $R_2$ independently of one another are hydrogen, fluorine, chlorine, bromine, methyl, ethyl, trifluoromethyl, methoxy, ethoxy or difluoromethoxy; $R_3$ is cyclopropyl or cyclopropyl which is substituted by one or two identical or different methyl or halogen groups; $R_4$ is halogen, $-SR_5$, $-OR_5$ or $-NR_5R_6$; and $R_5$ is hydrogen or a $C_1$-$C_4$alkyl group, which is unsubstituted or substituted by halogen, hydroxyl, $C_1$-$C_4$alkoxy, $C_1$-$C_4$alkylamino, bis($C_1$-$C_4$alkyl)amino or cyclopropyl or by $-COOC_1$-$C_3$alkyl; or in which $R_5$ is $C_3$-$C_4$alkenyl or $C_3$-$C_4$alkinyl, or a phenyl group which is unsubstituted or substituted by halogen, methyl or methoxy, or an acyl radical of the meaning g); and $R_6$ is hydrogen or a $C_1$-$C_4$alkyl group, which is unsubstituted or substituted by halogen, hydroxyl, $C_1$-$C_4$alkoxy, $C_1$-$C_4$alkylamino or bis($C_1$-$C_4$alkyl)amino, or in which $R_6$ is $C_3$-$C_4$alkenyl or $C_3$-$C_4$alkinyl (=compound group Ic).

Amongst these compounds of the formula Ic, those in which $R_1$ and $R_2$ are hydrogen, fluorine or difluoromethoxy, $R_3$ is cyclopropyl, $R_4$ is halogen, $-OR_5$ or $-NR_5R_6$ and $R_5$ is hydrogen or $R_6$, and $R_6$ is $C_1$-$C_3$alkyl, which is unsubstituted or monosubstituted by $C_1$-$C_4$alkoxy or cyclopropyl or substituted by up to 5 halogen atoms; or $C_3$-$C_4$alkenyl or alkinyl (=compound group Id), are preferred.

Amongst the latter, those compounds in which $R_1$ and $R_2$ independently of one another are hydrogen, 3-fluoro, 4-fluoro or 5-fluoro are preferred (=compound group Idd).

Another preferred group comprises the following compounds of the formula I in which $R_1$ and $R_2$ independently of one another are hydrogen, halogen, $C_1$-$C_3$alkyl, $C_1$-$C_2$halogenoalkyl, $C_1$-$C_3$alkoxy or $C_1$-$C_3$halogenoalkoxy; $R_3$ is $C_3$-$C_4$cycloalkyl, which is unsubstituted or monosubstituted by methyl or halogen; and $R_4$ is halogen (compound group Ie).

Amongst the abovementioned compounds, those in which $R_1$ and $R_2$ independently of one another are hydrogen or fluorine are preferred (=compound group Iee). Those in which $R_1$ and $R_2$ independently of one another are hydrogen, 3-fluoro, 4-fluoro or 5-fluoro are particularly preferred.

The compounds of the formula I are prepared by 1a) reacting a phenylguanidine salt of the formula IIa

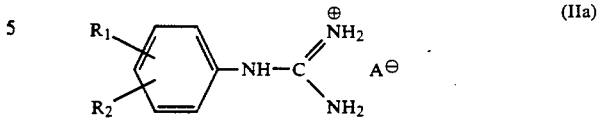

or the guanidine of the formula IIb on which this salt is based

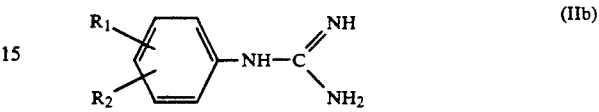

with a β-keto ester of the formula III

in which $R_1$, $R_2$ and $R_3$ are as defined for formula I and $R_7$ is $C_3$-$C_6$alkenyl, $C_3$-$C_6$alkinyl, benzyl which is unsubstituted or substituted by halogen and/or $C_1$-$C_3$alkyl or $C_1$-$C_8$alkyl, without a solvent or in a solvent, preferably in a protic solvent, at temperatures of 60° C. to 160° C., preferably 60° C. to 110° C., to give the compound Ia:

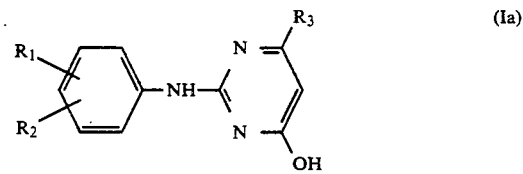

and, if desired, replacing the OH group by halogen to give compounds of the formula Ib

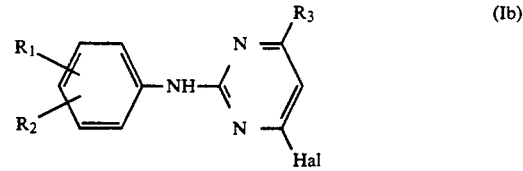

and, if desired, replacing the halogen atom further by one of the other groups mentioned for $R_4$, as explained below.

1b) The compound Ia is also obtained in a multi-stage process by another process variant, by reacting an isothiuronium salt of the formula IV

in which $A^\ominus$ is any desired anion, such as chloride, sulfate, phosphate and the like, and $R_8$ is $C_1$-$C_8$alkyl or benzyl which is unsubstituted or substituted by halogen and/or $C_1$-$C_4$alkyl, with a β-keto ester of the formula III preferably in a solvent, at temperatures from 40° C.

to 140° C., preferably at 60° C. to 100° C., the thiopyrimidine V being formed.

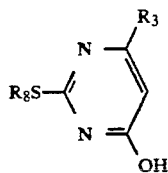

The resulting compound of the formula V is oxidized with an oxidizing agent, for example with a peracid, to give the pyrimidine compound of the formula VI

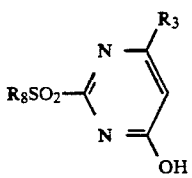

and this is reacted with formylaniline of the formula VII

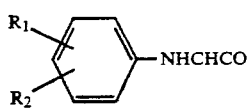

in an inert solvent in the presence of a base as a proton acceptor at temperatures between −30° C. and +120° C. to give a compound of the formula VIII

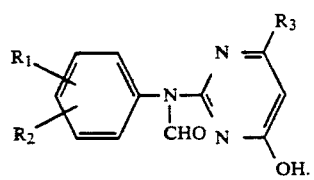

The resulting compound VIII is subjected to hydrolysis in the presence of a base, for example alkali metal hydroxide, or an acid, for example hydrohalic acid or sulfuric acid, in water or aqueous solvent mixtures, such as aqueous alcohols or dimethylformamide, at temperatures of 10° C. to 110° C., preferably 30° C. to 60° C., and then gives the compound of the formula Ia.

The compound Ib is obtained by replacing hydroxyl in compound Ia by halogen:

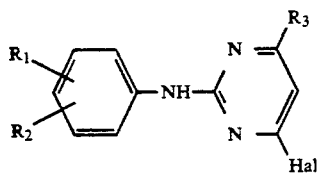

This is effected with halogen compoounds of tri- or pentavalent phosphorus in the presence or absence of a proton acceptor, for example diethylaniline, phosphorus oxyhalides preferably being employed. The reactions are carried out in an inert solvent or without a solvent at temperatures between 60° C. and 140° C., preferably 70° C. and 120° C.

The other compounds of the formula I in which $R_4$ has a meaning other than —OH or halogen are obtained by reaction of a compound of the formula Ib with a compound

These reactions can be carried out in an inert solvent. If the reactants are alcohols, these can be used as the solvent. Proton acceptors are necessary with the compounds IX and X, for which, for example, alkali metal or alkaline earth metal hydroxides, the alkali metal or alkaline earth metal salt of IX or X or metal hydrides are used.

If XI or XII is used, an excess of the corresponding amine can furthermore be used as the proton acceptor.

The reactions in these cases are carried out at −30° C. to +140° C., preferably at −10° C. to +110° C.

If in formula I $$R_5 = \overset{O}{\underset{\|}{C}}-R',$$

acid halides XIII

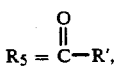     (XIII)

or acid anhydrides XIV

     (XIV)

are preferably used for the reactions.

If in formula I $$R_5 = -\overset{O}{\underset{\|}{C}}-NH-R'' \text{ or } -\overset{O}{\underset{\|}{C}}OR''$$

either isocyanates XV

R''NCO     (XV)

formyl halides XVI or formic anhydrides XVII are reacted:

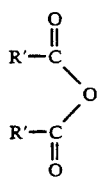

The present invention relates to the preparation processes described, including all the part steps.

Surprisingly, it has now been found that compounds of the formula I have a biocidal spectrum which is very favourable for practical requirements for controlling insects and phytopathogenic microorganisms, in particular fungi. They have very advantageous curative, preventive and in particular systemic properties and are employed for the protection of numerous crop plants. Using the active substances of the formula I, the pests which occur on plants or parts of plants (fruit, blossom, foilage, stems, tubers, roots) of various useful crops can be suppressed or destroyed, parts of plants which grow later also remaining protected, for example from phytopathogenic microorganisms.

Compounds of the formula I are active, for example, against the phytopathogenic fungi belonging to the following classes: Fungi imperfecti (in particular Botrytis, and futhermore Pyricularia, Helminthosporium, Fusarium, Septoria, Cercospora and Alternaria); and Basidiomycetes (for example Rhizoctonia, Hemilaeia and Puccinia). They are moreover active against the class of Ascomycetes (for example Venturia and Erysiphe, Podosphaera, Monilinia and Uncinula) and Oomycetes (for example Phytophthora, Pythium, Plasmopara). The compounds of the formula I can furthermore be employed as dressing compositions for the treatment of seed material (fruit, tubers, seeds) and plant seedlings for protection from fungal infections and against phytopathogenic fungi which occur in the soil.

The invention also relates to the compositions which contain compounds of the formula I as the active substance component, in particular plant protection compositions, and their use in the agricultural sector or related fields.

The present invention moreover also relates to the preparation of these compositions, which comprises intimately mixing the active substance with one or more of the substances or substance groups described in this Application. It also relates to a method for the treatment of plants, which is distinguished by application of the novel compounds of the formula I or the novel agents.

Examples of target crops for the plant protection use disclosed in the Application are, in the context of this invention, the following species of plants: cereals (wheat, barley, rye, oats, rice, maize, sorghum and related species); beet (sugar and feed beet); pomaceous, stone and soft fruit (apples, pears, plums, peaches, almonds, cherries, strawberries, raspberries and blackberries); pulses (beans, lentils, peas and soya); oil crops (rape, mustard, poppy, olive, sunflower, coconut, castor, cacao and peanut); cucumber plants (pumpkins, cucumbers and melons); fibre plants (cotton, flax, hemp and jute); citrous fruits (oranges, lemons, grapefruits and mandarins); vegetable varieties (spinach, lettuce, asparagus, cabbage varieties, carrots, onions, tomatoes, potatoes and paprika); laural plants (avocado, cinnamonium and camphor) or plants such as tobacco, nuts, coffee, sugar-cane, tea, pepper, vines, hops, banana and natural rubber plants and ornamental plants.

The active substances of the formula I are usually used in the form of compositions and can be applied to the area or plants to be treated at the same time as or after other active substances. These other active substances can be either fertilizers, suppliers of trace elements or other preparations which influence plant growth. They can also be selective herbicides as well as insecticides, fungicides, bactericides, nematicides, molluscicides or mixtures of several of these preparations, if appropriate together with other carriers, surfactants or other application-promoting additives conventionally used in the art of formulation.

Suitable carriers and additives can be solid or liquid and correspond to the substances which are suitable in the art of formulation, for example naturally occurring or regenerated mineral substances, solvents, dispersants, wetting agents, tackifiers, thickeners, binders or fertilizers.

A preferred method for application of an active substance of the formula I or an agrochemical composition containing at least one of these active substances is application to the foliage (leaf application). The application frequency and amount applied here depend on the pressure of infestation by the pathogen in question. However, the active substances of the formula I can also enter the plants through the root system via the soil (systemic action), by impregnating the location of the plant with a liquid formulation or introducing the substances into the soil in solid form, for example in the form of granules (soil application). In paddy rice crops, such granules can be metered into the flooded rice field. However, the compounds of the formula I can also be applied to seeds (coating), by either soaking the seeds in a liquid formulation of the active substance or coating them with a solid formulation.

The compounds of the formula I are employed here in unchanged form or, preferably, together with the auxiliaries conventionally used in the art of formulation. For this, they are advantageously processed in a known manner to, for example, emulsion concentrates, brushable pastes, directly sprayable or dilutable solutions, dilute emulsions, wettable powders, soluble powders, dust or granules, or by encapsulation in, for example, polymeric substances. The use methods, such as spraying, misting, dusting, scattering, brushing or pouring, like the nature of the composition, are chosen according to the intended aims and the given circumstances. Favourable application amounts are in general 50 g to 5 kg of active substance (AS) per hectare, preferably 100 g to 2 kg of AS/hectare, in particular 200 g to 600 g of AS/hectare.

The formulations, that is to say the compositions, preparations or combinations containing the active substance of the formula I and if appropriate a solid or liquid additive, are prepared in a known manner, for example by intimate mixing and/or grinding of the active substances with extenders, for example with solvents, solid carriers and if appropriate surface-active compounds (surfactants).

Possible solvents are: aromatic hydrocarbons, preferably $C_8$ to $C_{12}$ fractions, for example xylene mixtures or substituted naphthalenes, phthalic acid esters, such as dibutyl or dioctyl phthalate, aliphatic hydrocarbons, such as cyclohexane or paraffins, alcohols and glycols and ethers and esters thereof, such as ethanol, ethylene glycol or ethylene glycol monomethyl or ethyl ether, ketones, such as cyclohexanone, strongly polar solvents, such as N-methyl-2-pyrrolidone, dimethyl sulfoxide or dimethylformamide, and if appropriate epoxidized vegetable oils, such as epoxidized coconut oil or soya oil; or water.

Solid carriers which are used, for example for dusts and dispersible powders, are as a rule naturally occurring rock powders, such as calcite, talc, kaolin, montmorillonite or attapulgite. It is also possible to add highly disperse silicic acid or highly disperse absorbent polymers to improve the physical properties. Possible granular adsorptive granule carriers are porous types, for example pumice, broken brick, sepiolite or bentonite, and possible non-adsorptive carrier materials are, for example, calcite or sand. A number of pregranulated materials of inorganic nature, such as, in particular, dolomite, or comminuted plant residues can moreover be used.

Possible surface-active compounds are, depending on the nature of the active substance of the formula I to be formulated, nonionic, cationic and/or anionic surfactants having good emulsifying, dispersing and wetting properties. Surfactants are also to be understood as meaning surfactant mixtures.

Suitable anionic surfactants can be either so-called water-soluble soaps or water-soluble synthetic surface-active compounds.

Examples which may be mentioned of nonionic surfactants are nonylphenol-polyethoxyethanols, castor oil polyglycol ethers, polypropylene-polyethyleneoxy adducts, tributylphenoxypolyethylene-ethanol, polyethylene glycol and octylphenoxypolyethoxyethanol.

Fatty acid esters of polyoxyethylenesorbitan, such as polyoxyethylenesorbitan trioleate, are furthermore also possible.

The cationic surfactants are in particular quaternary ammonium salts which contain at least one alkyl radical having 8 to 22 C atoms as N-substituents and lower non-halogenated or halogenated alkyl, benzyl or lower hydroxyalkyl radicals as further substituents.

Other surfactants which are customary in the art of formulation are known to the expert or can be found in the relevant technical literature. The agrochemical formulations as a rule contain 0.1 to 99%, in particular 0.1 to 95%, of active substance of the formula I, 99.9 to 1%, in particular 99.8 to 5%, of a solid or liquid additive and 0 to 25%, in particular 0.1 to 25%, of a surfactant.

While concentrated compositions are more preferable as commercial goods, the final consumer as a rule uses dilute compositions.

The compositions can also contain other additives, such as stabilizers, foam suppressants, viscosity regulators, binders, tackifiers and fertilizers or other active substances for achieving specific effects.

The following examples serve to illustrate the invention in more detail without limiting it.

PREPARATION EXAMPLES

EXAMPLE 1

Preparation of 2-phenylamino-4-hydroxy-6-cyclopropyl-pyrimidine of the formula

[compound no. 2.1]

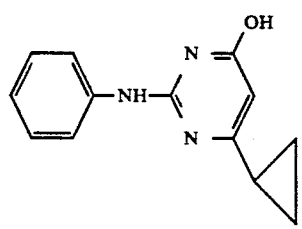

19.7 g (0.1 mol) of phenylguanidinium bicarbonate and 15.6 g (0.1 mol) of ethyl 3-cyclopropyl-3-oxopropionate in 100 ml of ethanol are refluxed for 16 hours, while stirring, a reddish-coloured solution forming with formation of carbon dioxide. After cooling to room temperature, the solution is treated with active charcoal and filtered and 400 ml of water are added to the filtrate. The grey powder which has separated out is purified by column chromatography over silica gel (methanol/chloroform 1:1). After evaporation of the mobile phase mixture, a white crystalline powder remains; melting point 234°–235° C. Yield 16.6 g (73 mmol; 73% of theory).

EXAMPLE 2

Preparation of 2-phenylamino-4-chloro-6-cyclopropylpyrimidine of the formula

[compound no. 1.1]

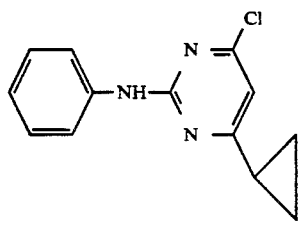

19.6 g (86.3 mmol) of 2-phenylamino-4-hydroxy-6-cyclopropyl-pyrimidine are added to 50 ml (0.55 mol) of phosphorus oxychloride at 75° C. in the course of one hour, while stirring, and the mixture is then refluxed for one hour. When the evolution of hydrogen chloride has ended, the reaction mixture is cooled to room temperature and poured into 200 ml of water, while stirring vigorously, the temperature being kept at about 50° C. by addition of ice. The approximately 400 ml of the pale brown suspension is brought to pH 7 by slow dropwise addition of 220 ml of 30% aqueous sodium hydroxide solution and is extracted three times with 150 ml of ethyl acetate each time. The combined extracts are washed twice with 100 ml of water each time, dried over sodium sulfate and filtered and the solvent is evaporated. The 20.7 of pale brown powder are treated with 400 ml of diethyl ether and the undissolved material is filtered off. After evaporation of the diethyl ether, the residue is recrystallized from diisopropyl ether. The yellowish crystals melt at 127°–128° C. Yield 17.7 g (72.1 mmol; 83.5% of theory).

EXAMPLE 3

Preparation of 2-phenylamino-4-methoxy-6-cyclopropylpyrimidine of the formula

[compound no. 2.3.]

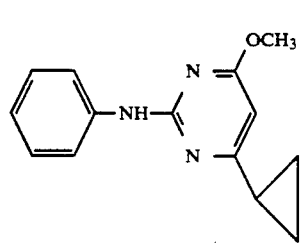

6.87 g (28 mmol) of 2-phenylamino-4-chloro-6-cyclopropyl-pyrimidine in 25 ml of dioxane are added dropwise to 5.8 g (32.2 mmol) of sodium methylate in 10 ml of absolute methanol at room temperature in the course of half an hour, while stirring, and the mixture is then heated at 50° C. for 6 hours. To bring the reaction to completion, a further 0.76 g (4.2 mmol) of sodium methylate is added and the mixture is heated at 50° C. for a further 20 hours. After evaporation of the solvent, 300 ml of diethyl ether are added to the residue, the suspension is washed twice with 100 ml of water each time and then dried over sodium sulfate and filtered and the diethyl ether is evaporated off. 6.7 g of yellow oil which remain are purified by column chromatography over silica gel using toluene as the mobile phase. After evaporation of the toluene, a pale yellow oil of refractive index $n_D^{25}$: 1.6225 remains. Yield: 5.8 g (24 mmol; 86% of theory).

EXAMPLE 4

Preparation of 2-phenylamino-4-dimethylamino-6-cyclopropylpyrimidine of the formula

[compound no. 3.1]

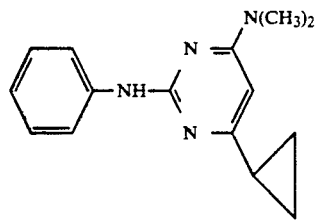

17.9 ml of 33% (100 mmol) absolute ethanolic dimethylamine solution are added dropwise to 9.8 g (40 mmol) of 2-phenylamino-4-chloro-6-cyclopropylpyrimidine in 20 ml of absolute ethanol at room temperature in the course of 10 minutes, while stirring, and the yellow suspension formed is heated at 50° C. for one hour and then refluxed for a further hour. After evaporation of the solvent, the residue is taken up in 200 ml of methylene chloride and the mixture is washed twice with 100 ml of water each time, dried over sodium sulfate, filtered and freed from the methylene chloride by evaporation. The 10.2 g of a yellow oil which remain are purified by column chromatography over silica gel using methylene chloride as the mobile phase. After evaporation of the methylene chloride, a pale yellow oil remains, which crystallizes after some hours. The pale yellow crystals melt at 90°-91° C. Yield: 8.9 g (35 mmol; 87.5% of theory).

The following compounds are obtained in this manner or by one of the other methods described above.

TABLE 1

Compounds of the formula

| Compound No. | $R_1$ | $R_2$ | $R_3$ | Physical constants |
|---|---|---|---|---|
| 1.1 | H | H | Cl | m.p. 127-128° C. |
| 1.2 | 4-F | H | Cl | m.p. 142-144° C. |
| 1.3 | 3-F | H | Cl | m.p. 133-134° C. |
| 1.4 | H | H | $-SCH_3$ | m.p. 99-100° C. |
| 1.5 | H | H | Br | m.p. 132-133° C. |
| 1.6 | H | H | $-SCN$ | m.p. 104-105° C. |
| 1.7 | H | H | $-SC_2H_5$ | |
| 1.8 | H | H | F | m.p. 123-124° C. |
| 1.9 | 3-F | 5-F | Cl | |
| 1.10 | 3-F | H | F | m.p. 144.5-147° C. |
| 1.11 | 3-F | H | Br | m.p. 137-139° C. |
| 1.12 | 4-F | H | F | m.p. 151-153° C. |
| 1.13 | H | H | I | m.p. 141-144° C. |
| 1.14 | 4-F | H | Br | m.p. 142-145° C. |

TABLE 2

Compounds of the formula

| Compound No. | $R_1$ | $R_2$ | $R_4$ | Physical constants |
|---|---|---|---|---|
| 2.1 | H | H | $-OH$ | m.p. 234-235° C. |
| 2.2 | 4-F | H | $-OCH_3$ | m.p. 91.5-93° C. |
| 2.3 | H | H | $-OCH_3$ | Oil: $n_D^{25}$: 1.6225 |
| 2.4 | H | H | $-OCHF_2$ | m.p. 55-57° C. |
| 2.5 | 3-F | H | $-OCH_3$ | |
| 2.6 | H | H | $-OCH_2-C\equiv CH$ | m.p. 84-85° C. |
| 2.7 | H | H | $-OCH_2CH_3$ | m.p. 62.5-63° C. |
| 2.8 | H | H | $-O-\underset{\underset{O}{\|}}{C}CH_3$ | |
| 2.9 | H | H | $-OCH_2CH_2N(CH_3)_2$ | Oil: $n_D^{20}$: 1.5977 |
| 2.10 | H | H | $-OCH_2CH=CH-CH_3$ | Oil; $n_D^{20}$: 1.6079 |
| 2.11 | 4-$CH_3$ | H | $-OCH_3$ | |

TABLE 2-continued

Compounds of the formula

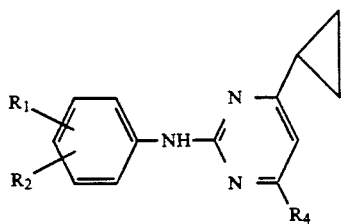

| Compound No. | $R_1$ | $R_2$ | $R_4$ | Physical constants |
|---|---|---|---|---|
| 2.12 | H | H | —OC(=O)NHCH$_3$ | m.p. 233–236 |
| 2.13 | H | H | —OCF$_2$CHF$_2$ | m.p. 72–74° C. |
| 2.14 | 4-F | H | —OH | m.p. >250° C. |
| 2.15 | 4-OCHF$_2$ | H | —OCH$_3$ | |
| 2.16 | H | H | —OCH$_2$CH$_2$OCH$_3$ | m.p. 91–92° C. |
| 2.17 | 4-CF$_3$ | H | —OCH$_3$ | |
| 2.18 | H | H | —O—C$_6$H$_4$—CH$_3$ (para) | Oil; $n_D^{20}$: 1.6278 |
| 2.19 | H | H | —OCF$_2$CClFCF$_2$CHClF | m.p. 40–41° C. |
| 2.20 | 4-F | H | —OC(=O)CH$_3$ | |
| 2.21 | H | H | —O—CH$_2$—C$_6$H$_3$(OCH$_3$)$_2$ | m.p. 140–141° C. |
| 2.22 | H | H | —OCH(CH$_3$)CH$_2$CH$_3$ | Oil; $n_D^{20}$: 1.5902 |
| 2.23 | H | H | —OCH(CH$_3$)CH$_2$OCH$_3$ | Oil; $n_D^{20}$: 1.5908 |
| 2.24 | 4-OCH$_3$ | H | —OCH$_3$ | |
| 2.25 | H | H | —OC(=O)OCH$_3$ | Oil; $n_D^{20}$: 1.6005 |
| 2.26 | H | H | —OCH$_2$CF$_3$ | m.p. 89–90° C. |
| 2.27 | H | H | —OC(=O)CH$_2$Cl | |
| 2.28 | H | H | —OC$_3$H$_7$-i | Oil; $n_D^{30}$: 1.5971 |
| 2.29 | H | H | —OC(=O)CH$_2$OCH$_3$ | |
| 2.30 | 3-OCHF$_2$ | H | —OCH$_3$ | |
| 2.31 | 3-F | 5-F | —OCH$_3$ | |
| 2.32 | H | H | —OCF$_2$CHClF | m.p. 37–39° C. |
| 2.33 | 3-F | H | —OH | m.p. 179–185° C. |

TABLE 3

Compounds of the formula

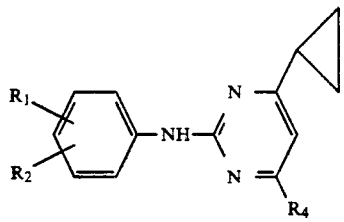

| Compound No. | $R_1$ | $R_2$ | $R_4$ | Physical constants |
|---|---|---|---|---|
| 3.1 | H | H | —N(CH₃)₂ | m.p. 90–91° C. |
| 3.2 | H | H | —NH₂ | m.p. 114–115° C. |
| 3.3 | H | H | —NHC₂H₅ | Oil; $n_D^{30}$: 1.6360 |
| 3.4 | H | H | —NHC(O)CH₂Cl | |
| 3.5 | H | H | —N(morpholino) | m.p. 142–143° C. |
| 3.6 | H | H | —NHCH₂CH₂OH | Viscous mass |
| 3.7 | H | H | —NHCH₃ | Oil; $n_D^{20}$: 1.6478 |
| 3.8 | 3-F | H | —N(CH₃)₂ | |
| 3.9 | H | H | —NH-cyclopropyl | m.p. 100.5–101.5° C. |
| 3.10 | H | H | —N(CH₂CH₂OH)₂ | m.p. 94–95° C. |
| 3.11 | H | H | —HN—C(O)—C₆H₄—Cl | |
| 3.12 | H | H | —NHCH₂—C₆H₅ | Oil; $n_D^{50}$: 1.6437 |
| 3.13 | H | H | —HN—C(O)—(2,6-dichloropyridin-4-yl) | |
| 3.14 | H | H | —NHCH₂CH₂CH₃ | Oil; $n_D^{20}$: 1.6294 |
| 3.15 | H | H | —NH(CH₂)₇CH₃ | Oil; $n_D^{20}$: 1.5881 |
| 3.16 | 4-F | H | —N(CH₃)₂ | |
| 3.17 | H | H | —NHCH₂C(O)OC₂H₅ | m.p. 113–115° C. |
| 3.18 | H | H | —NHCH₂CH₂OCH₃ | m.p. 109.5–111° C. |
| 3.19 | H | H | —NHCH(CH₃)CH₂OH | Oil; $n_D^{50}$: 1.6173 |
| 3.20 | 3-F | H | —N(CH₂CH=CH₂)₂ | |
| 3.21 | H | H | —N(CH₃)CH₂CH₂CN | m.p. 143–147° C. |

TABLE 3-continued

Compounds of the formula

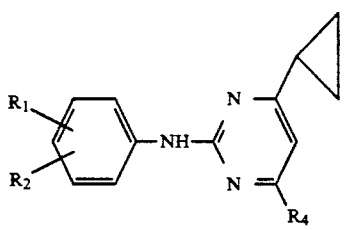

| Compound No. | R$_1$ | R$_2$ | R$_4$ | Physical constants |
|---|---|---|---|---|
| 3.22 | H | H | —NH(CH$_2$)$_3$N(CH$_3$)$_2$ | Oil; n$_D^{20}$: 1.6160 |
| 3.23 | H | H | —N(CH$_3$)—CH$_2$—C$_6$H$_5$ | m.p. 120–121° C. |
| 3.24 | H | H | —NH(CH$_2$—CH=CH$_2$) | |
| 3.25 | H | H | —NH—CH$_2$CH(CH$_3$)—C$_2$H$_5$ | Viscous mass |
| 3.26 | H | H | —N(piperidyl) | m.p. 151–153° C. |
| 3.27 | H | H | —NHCH$_2$CH(OH)—CH$_2$OH | m.p. 185–186° C. |
| 3.28 | H | H | —NH—cyclopentyl | Oil; n$_D^{50}$: 1.6255 |
| 3.29 | H | H | —NH—C$_6$H$_4$—F | m.p. 114–116° C. |
| 3.30 | H | H | —NH(CH$_2$)$_2$N(C$_4$H$_9$-n)$_2$ | Viscous mass |
| 3.31 | H | H | —NHCH$_2$-(2-furyl) | Oil; n$_D^{20}$: 1.6476 |
| 3.32 | H | H | —NHCH$_2$—C≡CH | m.p. 104–105° C. |
| 3.33 | H | H | —NH—cyclohexyl | Oil; n$_D^{50}$: 1.6103 |
| 3.34 | H | H | —NH—C$_6$H$_5$ | m.p. 119–120° C. |
| 3.35 | H | H | —N(1,2,4-triazolyl) | m.p. 202–203° C. |

TABLE 3-continued
Compounds of the formula
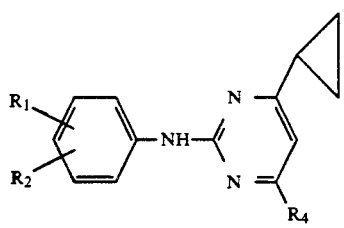
| Compound No. | R₁ | R₂ | R₄ | Physical constants |
|---|---|---|---|---|
| 3.36 | H | H | –N(CH₃)–C₆H₅ | m.p. 209–210° C. |
| 3.37 | H | H | 2,6-dimethylmorpholino | |
| 3.38 | H | H | –N(CH₂CH₂OH)–CH₂–C₆H₅ | m.p. 117–118° C. |
| 3.39 | H | H | –NHCH₂CH₂N(C₂H₅)₂ | Viscous mass |
| 3.40 | H | H | –NH(CH₂)₃OCH₃ | m.p. 80–83° C. |
| 3.41 | H | H | –N(aziridinyl) | m.p. 92–95° C. |
| 3.42 | 3-F | H | –N(aziridinyl) | |
| 3.43 | 4-F | H | –N(aziridinyl) | |
| 3.44 | 3-F | 4-F | –N(aziridinyl) | |
| 3.45 | 3-F | 5-F | –N(aziridinyl) | |
| 3.46 | H | H | –NH–CO–NH–CH₃ | m.p. 164–166° C. |
| 3.47 | H | H | –NH–COOCH₃ | m.p. 216–217° C. |

TABLE 4
Compounds of the formula
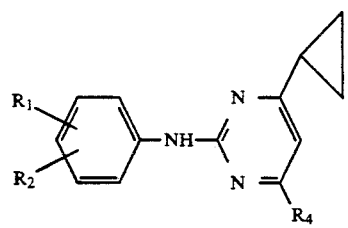
| Compound No. | $R_1$ | $R_2$ | $R_3$ | $R_4$ | Physical constants |
|---|---|---|---|---|---|
| 4.1 | H | H | ⟨▷⟩-CH₃ | Cl | m.p. 124–127° C. |
| 4.2 | 3-F | H | ⟨▷⟩-CH₃ | Cl | |
| 4.3 | H | H | Cyclobutyl | Cl | |
| 4.4 | H | H | Cyclohexyl | Cl | |
| 4.5 | 4-F | H | ⟨▷⟩-CH₃ | Cl | m.p. 146–149° C. |
| 4.6 | H | H | ⟨▷⟩-F | Cl | |
| 4.7 | H | H | Cyclobutyl | —OCH₃ | |
| 4.8 | H | H | ⟨▷⟩-CH₃ | —OCH₃ | Oil; $n_D^{25}$: 1.6232 |
| 4.9 | 4-F | H | ⟨▷⟩-Cl | —OCH₃ | |
| 4.10 | 4-F | H | ⟨▷⟩-CH₃ | —OCH₃ | m.p. 85–88° C. |
| 4.11 | 4-F | H | Cyclobutyl | —OCH₃ | |
| 4.12 | H | H | Cyclohexyl | —OCH₃ | |
| 4.13 | 3-F | H | ⟨▷⟩-CH₃ | —OCH₃ | |
| 4.14 | H | H | ⟨▷⟩-Cl | —OCH₃ | |
| 4.15 | 3-F | H | ⟨▷⟩-Cl | —OCH₃ | |

TABLE 4-continued

Compounds of the formula

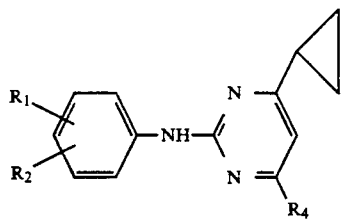

| Compound No. | R₁ | R₂ | R₃ | R₄ | Physical constants |
|---|---|---|---|---|---|
| 4.16 | H | H | ▷−CH₃ | −N(CH₃)₂ | m.p. 88–91° C. |
| 4.17 | 3-F | H | ▷−CH₃ | −N(CH₃)₂ | |
| 4.18 | H | H | ▷−Cl | −N(CH₃)₂ | |
| 4.19 | 4-F | H | ▷−CH₃ | −N(CH₃)₂ | |
| 4.20 | H | H | Cyclobutyl | −N(CH₃)₂ | |
| 4.21 | H | H | Cyclohexyl | −N(CH₃)₂ | |

2. Formulation examples for liquid active compounds of the formula I (%=percent by weight)

| 2.1. Emulsion concentrates | a) | b) | c) |
|---|---|---|---|
| Active substance from the table | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from such concentrates by dilution with water.

| 2.2. Solutions | a) | b) | c) | d) |
|---|---|---|---|---|
| Active substance from the table | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Benzine (boiling range 160–190° C.) | — | — | 94% | — |

(MW = molecular weight)

The solutions are suitable for use in the form of tiny drops.

| 2.3. Granules | a) | b) |
|---|---|---|
| Active substance from the table | 5% | 10% |
| Kaolin | 94% | — |
| Highly disperse silicic acid | 1% | — |
| Attapulgite | — | 90% |

The active substance is dissolved in methylene chloride, the solution is sprayed onto the carrier and the solvent is then evaporated in vacuo.

| 2.4. Dusts | a) | b) |
|---|---|---|
| Active substance from the table | 2% | 5% |
| Highly disperse silicic acid | 1% | 5% |
| Talc | 97% | — |
| Kaolin | — | 90% |

Ready-to-use dusts are obtained by intimate mixing with the active substance on the carriers.

Formulation examples for solid active substances of the formula I (%=percent by weight)

| 2.5. Wettable powders | a) | b) | c) |
|---|---|---|---|
| Active substance from the table | 25% | 50% | 75% |
| Na ligninsulfonate | 5% | 5% | — |
| Na lauryl sulfate | 3% | — | 5% |
| Na diisobutylnaphthalenesulfonate | — | 6% | 10% |
| Octylphenol polyethylene glycol ether (7–8 mol of ethylene oxide) | — | 2% | — |

| 2.5. Wettable powders | a) | b) | c) |
|---|---|---|---|
| Highly disperse silicic acid | 5% | 10% | 10% |
| Kaolin | 62% | 27% | — |

The active substance is mixed thoroughly with the additives and the mixture is ground thoroughly in a suitable mill. Wettable powders which can be diluted with water to give suspensions of any desired concentration are obtained.

| 2.6. Emulsion concentrate | |
|---|---|
| Active substance from the table | 10% |
| Octylphenol polyethylene glycol ether (4–5 mol of ethylene oxide) | 3% |
| Ca dodecylbenzenesulfonate | 3% |
| Castor oil polyglycol ether (35 mol of ethylene oxide) | 4% |
| Cyclohexanone | 34% |
| Xylene mixture | 50% |

Emulsions of any desired concentration can be prepared from this concentrate by dilution with water.

| 2.7. Dusts | a) | b) |
|---|---|---|
| Active substance from the table | 5% | 8% |
| Talc | 95% | — |
| Kaolin | — | 92% |

Ready-to-use dusts are obtained by mixing the active substance with the carrier and grinding the mixture on a suitable mill.

| 2.8. Extruded granules | |
|---|---|
| Active substance from the table | 10% |
| Na ligningsulfonate | 2% |
| Carboxymethylcellulose | 1% |
| Kaolin | 87% |

The active substance is mixed with the additives and the mixture is ground and moistened with water. This mixture is extruded and then dried in a stream of air.

| 2.9. Coated granules | |
|---|---|
| Active substance from the table | 3% |
| Polyethylene glycol (MW 200) | 3% |
| Kaolin | 94% |

(MW = molecular weight)

The finely ground active substance is applied uniformly to the polyethylene glycol-moistened kaolin in a mixer. Dust-free coated granules are obtained in this manner.

| 2.10. Suspension concentrate | |
|---|---|
| Active substance from the table | 40% |
| Ethylene glycol | 10% |
| Nonylphenol polyethylene glycol ether (15 mol of ethylene oxide) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |

| 2.10. Suspension concentrate | |
|---|---|
| Water | 32% |

The finely ground active substance is intimately mixed with the additives. A suspension concentrate is thus obtained, from which suspensions of any desired concentration can be prepared by dilution with water.

3. Biological examples

EXAMPLE 3.1

Action against Venturia inaequalis on apple shoots, residual-protective action

Apple seedlings with fresh shoots 10–20 cm long are sprayed with a spray liquor prepared from a wettable powder of the active substance (0.006% of active substance). After 24 hours, the treated plants are infected with a conidia suspension of the fungus. The plants are then incubated for 5 days at 90–100% relative atmospheric humidity and placed in a greenhouse at 20°–24° C. for a further 10 days. The scab attack is evaluated 15 days after the infection.

Compounds from Tables 1 to 4 have a good activity against Venturia (attack: less than 20%). Compounds no. 1.1, 1.13 and 2.2 thus reduce the Venturia attack to 0 to 5%. In contrast, untreated but infected control plants showed a Venturia attack of 100%.

EXAMPLE 3.2

Action against Botrytis cinerea on apple fruit. Residual-protective action

Artificially damaged apples are treated by dripping a spray liquor prepared from a wettable powder of the active substance (0.002% of active substance) onto the damaged areas. The treated fruits are then inoculated with a spore suspension of the fungus and incubated for one week at a high atmospheric humidity and about 20° C. For evaluation, the damaged areas which have started to rot are counted and the fungicidal action of the test substance is deduced therefrom.

Compounds from the tables have a good activity against Botrytis (attack: less than 20%). The compounds no. 1.1, 1.2, 1.3, 1.5, 1.10, 1.11, 1.12, 1.13, 1.14, 2.2, 2.3, 2.4, 2.13, 2.28, 3.1, 3.9, 3.21, 3.41, 4.1, 4.5, 4.8, 4.10, 4.16 and others, for example, thus reduced the Botrytis attack to 0 to 10%. In contrast, untreated but infected control plants exhibited a Botrytis attack of 100%.

EXAMPLE 3.3

Action against Erysiphae graminis on barley a) Residual-protective action

Barley plants about 8 cm high are sprayed with a spray liquor prepared from a wettable powder of the active substance (0.006% of active substance). After 3–4 hours, the treated plants are dusted with conidia of the fungus. The infected barley plants are placed in a greenhouse at about 22° C. and the fungal attack is evaluated after 10 days.

Compounds from the tables have a good activity against Erysiphae (attack: less than 20%). In contrast, untreated but infected control plants exhibit an Erysiphae attack of 100%.

EXAMPLE 3.4

Action against Helminthosporium gramineum

Wheat grains are contaminated with a spore suspension of the fungus and dried again. The contaminated grains are dressed with a suspension of the test substance prepared from a wettable powder (600 ppm of active substance, based on the weight of the seeds). After two days, the seeds are laid on suitable agar dishes and after a further four days the development of the fungal colonies around the seeds is evaluated. The number and size of the fungal colonies are used to evaluate the test substance. The compounds of Tables 1 to 4 substantially prevent fungal attack (0 to 10% fungal attack).

EXAMPLE 3.5

Action against Colletotrichum lagenarium on cucumbers

Cucumber plants are sprayed, after growing for 2 weeks, with a spray liquor prepared from a wettable powder of the active substance (concentration 0.002%). After 2 days, the plants are infected with a spore suspension ($1.5 \times 10^5$ spores/ml) of the fungus and incubated at 23° C. and a high atmospheric humidity for 36 hours. The incubation is then continued at normal atmospheric humidity and about 22°-23° C. The fungal attack which has occurred is evaluated 8 days after the infection. Untreated but infected control plants exhibit a fungal attack of 100%.

Compounds of the formula I from the tables show a good activity and prevent the spread of the disease attack. The fungal attack is suppressed to 20% or less.

What is claimed is:

1. A compound of the formula I

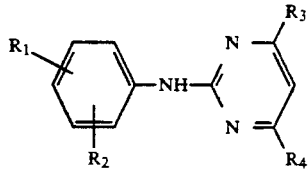

in which: $R_1$ and $R_2$ independently of one another are hydrogen, halogen, $C_1$-$C_3$alkyl, $C_1$-$C_2$halogenoalkyl, $C_1$-$C_3$alkoxy or $C_1$-$C_3$halogenoalkoxy; $R_3$ is $C_3$-$C_6$cycloalkyl or $C_3$-$C_6$cycloalkyl which is substituted by up to three identical or different methyl or halogen groups; $R_4$ is halogen, thiocyano(—SCN), —$OR_5$, or —$NR_5R_6$, in which $R_5$ a) is hydrogen, unsubstituted $C_1$-$C_8$alkyl or a $C_1$-$C_4$alkyl group which is substituted by halogen, hydroxyl, cyano, $C_1$-$C_4$alkoxy, $C_1$-$C_4$alkylamino, bis($C_1$-$C_4$alkyl)amino or $C_3$-$C_6$cycloalkyl or by substituted or unsubstituted phenyl or by —CO—$OC_1$-$C_3$alkyl; or b) is $C_3$-$C_6$cycloalkyl which is unsubstituted or substituted by methyl; or c) is $C_3$-$C_6$alkenyl which is unsubstituted or substituted by halogen; or d) is $C_3$-$C_6$alkinyl which is unsubstituted or substituted by halogen; or e) is phenyl which is unsubstituted or substituted by halogen, $C_1$-$C_3$alkyl, $C_1$-$C_3$alkoxy or nitro; or f) is a heterocyclic radical selected from the group consisting of imidazole, oxazole, thiazole, 1,2,4-triazole, pyrrole, pyrrolidine, piperidine, morpholine, thiomorpholine, 2,6-dimethylmorpholine, furan, tetrahydrofuran, thiophene, pyridine, picoline, pyrazine, triazine, oxazine and dioxane which can be bonded via —$CH_2$— and is unsubstituted or substituted by halogen, $C_1$-$C_3$alkyl, $C_1$-$C_3$alkoxy or nitro; or g) is an acyl radical —CO—R', in which R' is $C_1$-$C_6$alkyl which is unsubstituted or substituted by halogen or $C_1$-$C_3$alkoxy; $C_3$-$C_6$alkenyl which is unsubstituted or substituted by halogen; pyridine which is substituted by halogen or phenyl which is unsubstituted or substituted by halogen, $C_1$-$C_3$alkyl, $C_1$-$C_3$alkoxy or nitro; or h) is a carbamoyl radical —CO—NH—R" or an oxycarbonyl radical —CO—OR", in which R" is an aliphatic or cycloaliphatic radical having not more than 6 C atoms, which is unsubstituted or halogen-substituted, or in which R" is a phenyl or benzyl radical, which is in each case unsubstituted or substituted in the aromatic ring by halogen, $C_1$-$C_3$alkyl, $C_1$-$C_3$alkoxy or nitro;

and in which $R_6$ is hydrogen, unsubstituted $C_1$-$C_8$alkyl or $C_1$-$C_4$alkyl which is substituted by halogen, hydroxyl, cyano or $C_1$-$C_4$alkoxy; or in which $R_6$ is $C_3$-$C_6$cycloalkyl which is unsubstituted or substituted by methyl; $C_3$-$C_6$alkenyl or $C_3$-$C_6$alkinyl which is in each case unsubstituted or substituted by halogen; or phenyl which is unsubstituted or substituted by halogen, $C_1$-$C_3$alkyl, $C_1$-$C_3$alkoxy or nitro; and wherein, in the case where $R_4$ is $NR_5R_6$, the substituents $R_5$ and $R_6$, together with the N atom, can also together form an aziridine ring or an unsubstituted or alkyl substituted 5- or 6-membered heterocyclic radical selected from the group consisting of imidazole oxazole, thiazole, 1,2,4-triazole, pyrrole, pyrrolidine, piperidine, morpholine and thiomorpholine.

2. A compound according to claim 1, in which $R_1$ and $R_2$ independently of one another are hydrogen or fluorine.

3. A compound according to claim 1, in which $R_1$ and $R_2$ independently of one another are hydrogen, halogen, $C_1$-$C_3$alkyl, $C_1$-$C_2$halogenoalkyl, $C_1$-$C_3$alkoxy or $C_1$-$C_3$halogenoalkoxy; $R_3$ is $C_3$-$C_4$cycloalkyl, which is unsubstituted or monosubstituted by methyl or halogen; and $R_4$ is halogen, —$OR_5$ or —$NR_5R_6$, in which $R_5$ has the meanings a), b), c), d) or g) and $R_6$ is hydrogen or an alkyl, alkenyl or alkinyl radical, which can be unsubstituted or halogen-substituted if appropriate; or in which $R_5$ and $R_6$, together with the common N atom, are an aziridine ring or a piperidine or morpholine ring which is unsubstituted or methyl-substituted if appropriate.

4. A compound according to claim 3, in which $R_1$ and $R_2$ independently are hydrogen or fluorine.

5. A compound according to claim 1, in which: $R_1$ and $R_2$ independently of one another are hydrogen, fluorine, chlorine, bromine, methyl, ethyl, trifluoromethyl, methoxy, ethoxy or difluoromethoxy; $R_3$ is cyclopropyl or cyclopropyl which is substituted by one or two identical or different methyl or halogen groups; $R_4$ is halogen, —$SR_5$, —$OR_5$ or —$NR_5R_6$; and $R_5$ is hydrogen or a $C_1$-$C_4$alkyl group, which is unsubstituted or substituted by halogen, hydroxyl, $C_1$-$C_4$alkoxy, $C_1$-$C_4$alkylamino, bis($C_1$-$C_4$alkyl)amino or cyclopropyl or by —$COOC_1$-$C_3$alkyl; or in which $R_5$ is $C_3$-$C_4$alkenyl or $C_3$-$C_4$alkinyl, or a phenyl group which is unsubstituted or substituted by halogen, methyl or methoxy, or an acyl radical of the meaning g); and $R_6$ is hydrogen or a $C_1$-$C_4$alkyl group, which is unsubstituted or substituted by halogen, hydroxyl, $C_1$-$C_4$alkoxy, $C_1$-$C_4$alkylamino or bis($C_1$-$C_4$alkyl)amino, or in which $R_6$ is $C_3$-$C_4$alkenyl or $C_3$-$C_4$alkinyl.

6. A compound according to claim 5, in which $R_1$ and $R_2$ are hydrogen, fluorine or difluoromethoxy, $R_3$ is cyclopropyl, $R_4$ is halogen, $-OR_5$ or $-NR_5R_6$ and $R_5$ is hydrogen or $R_6$, and $R_6$ is $C_1$-$C_3$alkyl, which is unsubstituted or monosubstituted by $C_1$-$C_4$alkoxy or cyclopropyl or substituted by up to 5 halogen atoms; or $C_3$-$C_4$alkenyl or alkinyl.

7. A compound according to claim 6, in which $R_1$ and $R_2$ independently of one another are hydrogen, 3-fluorine, 4-fluorine or 5-fluorine.

8. A compound according to claim 1, in which $R_1$ and $R_2$ independently of one another are hydrogen, halogen, $C_1$-$C_3$alkyl, $C_1$-$C_2$halogenoalkyl, $C_1$-$C_3$alkoxy or $C_1$-$C_3$halogenoalkoxy; $R_3$ is $C_3$-$C_4$cycloalkyl, which is unsubstituted or monosubstituted by methyl or halogen; and $R_4$ is halogen.

9. A compound of claim 8 wherein $R_3$ is cyclopropyl.

10. A compound according to claim 8, in which $R_1$ and $R_2$ independently of one another are hydrogen or fluorine.

11. A compound of claim 10 wherein $R_3$ is cyclopropyl.

12. A compound according to claim 10, in which $R_1$ and $R_2$ independently of one another are hydrogen, 3-fluorine, 4-fluorine or 5-fluorine.

13. A microbicidal composition containing, besides customary carrier material, an effective amount of a compound of the formula I according to claim 1 as the active component.

14. A composition according to claim 13, where the active component is a compound of the formula I wherein $R_1$ and $R_2$ independently of one another are hydrogen, halogen, $C_1$-$C_3$-alkyl, $C_1$-$C_2$-halogenoalkyl, $C_1$-$C_3$alkoxy or $C_1$-$C_3$-halogenoalkoxy; $R_3$ is $C_3$-$C_4$-cycloalkyl which is unsubstituted or monosubstituted by methyl or halogen and $R_4$ is halogen.

15. A process for combating or preventing attack of crop plants by phytopathogenic microorganisms, wherein an effective amount of a compound of the formula I according to claim 1 is applied to the plants, to parts of the plants or to their location as the active compound.

16. A process according to claim 15, which comprises applying a compound of the formula I wherein $R_1$ and $R_2$ independently of one another are hydrogen, halogen, $C_1$-$C_3$-alkyl, $C_1$-$C_2$-halogenoalkyl, $C_1$-$C_3$alkoxy or $C_1$-$C_3$-halogenoalkoxy; $R_3$ is $C_3$-$C_4$-cycloalkyl which is unsubstituted or monosubstituted by methyl or halogen and $R_4$ is halogen.

17. A composition of claim 14 wherein $R_3$ is cyclopropyl.

18. A composition of claim 14 wherein $R_1$ and $R_2$ are independently of one another hydrogen or fluorine.

19. A process of claim 16 wherein $R_3$ is cyclopropyl.

20. A process of claim 16 wherein $R_1$ and $R_2$ are independently of one another hydrogen or fluorine.

* * * * *